United States Patent [19]

Warriner

[11] Plant 5,119

[45] Oct. 11, 1983

[54] ROSE PLANT 71-1172

[75] Inventor: William A. Warriner, Tustin, Calif.

[73] Assignee: Jackson & Perkins Company, Medford, Oreg.

[21] Appl. No.: 353,522

[22] Filed: Mar. 1, 1982

[51] Int. Cl.[3] ..... A01H 5/00

[52] U.S. Cl. ..... Plt./15

[58] Field of Search ..... Plt./15

*Primary Examiner*—Robert E. Bagwill

*Attorney, Agent, or Firm*—Klarquist, Sparkman, Campbell, Leigh, Whinston & Dellett

[57] ABSTRACT

A hybrid tea rose variety having a well branched, upright plant with stiff growth habit; glossy dark green foliage; yellow-orange pointed buds; large open flowers; little fragrance.

1 Drawing Figure

This present invention relates to a new and distinct variety of rose plant of the hybrid tea class which was originated by me by crossing the variety Golden Gate with an unnamed variety.

The primary objective of this breeding was to produce a new rose variety combining the flower color of Golden Gate and a plant of more profuse branching habit. This objective was substantially achieved along with other desirable improvements as evidenced by the following unique combination of characteristics which are outstanding in the new variety and which distinguish it from its parents as well as from all other varieties of which I am aware:

1. Upright, well branched, but stiff habit of growth.
2. Glossy dark green foliage that is reddish-purple when young.
3. Pointed flower buds of a yellow-orange 16C (RHS) color.
4. Large open flowers of essentially the same color as the buds.
5. Little or no fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated.

Parentage:
- *Seed parent.*—Golden Gate.
- *Pollen parent.*—Unnamed variety.

Classification:
- *Botanical.*—Rosa hybrid.
- *Commercial.*—Hybrid tea.

FLOWER

Observations made from specimens grown outdoors at Irvine, Calif. in October, 1981.

Blooming habit: Continuous.

Bud:
- *Size.*—$1\frac{1}{4}''$ when petals start to unfurl.
- *Form.*—Pointed ovoid.
- *Color.*—When sepals first divide, near Yellow-Orange 16C. When half blown; upper side of petals Yellow-Orange 16C, lower side of petals Yellow-Orange 16C.
- *Sepals.*—Color: Outer surface Green 138A, smooth. Three appendaged sepals lightly appendaged; two unappendaged sepals glandular edge.
- *Receptacle.*—Color: Green 139B. Shape: Funnel. Size: Large, long. Surface: Smooth.
- *Peduncle.*—Length: Short. Surface: Prickly. Color: Light green. Strength: Stiff, erect, heavy.
- *Opening.*—Petals fold out evenly.

Bloom:
- *Size.*—Very large. Average open size is 5" to 6".
- *Borne.*—Singly or several together.
- *Stems.*—Long, strong.
- *Form.*—When first open, high centered. Permanence: Outer petal edges slightly curled.
- *Petalage.*—Number of petals under normal conditions: 25.
- *Color.*—Center of flower: Upper side of petals, Yellow-Orange 16C; reverse side of petals, Yellow-Orange 16C; base of petals, Yellow-Orange 16C. General tonality from a distance: in ordinary terms, bright yellow, but very similar to RHS Color Chart Yellow-Orange 16C.
- *Variegations.*—None.
- *Discoloration.*—General tonality at end of first day, none; third day, slight fading only.
- *Fragrance.*—Slight.

Petals:
- *Texture.*—Thick.
- *Shape.*—Round.
- *Form.*—Tips slightly recurved.
- *Arrangement.*—Irregular. Petaloids in center, few.
- *Persistence.*—Drop off cleanly.
- *Lastingness.*—On the plant, long. As cut flower, long.

Reproductive parts:
- *Anthers.*—Large. Color: Yellow. Arrangement: Regular around styles.
- *Filaments.*—Color: Yellow.
- *Pollen.*—Gold yellow.
- *Styles.*—Color: White near base, red at distal half.
- *Stigmas.*—Color: Yellow.

PLANT

Form: Bush.

Growth: Upright, branching.

Foliage: Number of leaflets on normal mid-stem leaves: 5 or 7.

*Size.*—Large.

*Quantity.*—Normal.

*Color.*—New foliage: Greyed-Purple 184A aging to green when expanded. Old foliage: Dark green 139A.

Leaflets:

*Shape.*—Oval pointed.

*Texture.*—Upper side: Glossy.

*Edge.*—Serrated.

*Serration.*—Single, small.

*Petiole.*—Rachis: Color: Reddish. Underside: Prickles.

*Stipules.*—Long.

*Disease resistance.*—Normally resistant to mildew under normal growing conditions at Irvine, Calif.

Wood:

*New wood.*—Color: Light green. Bark: Smooth.

*Old wood.*—Color: Green. Bark: Smooth.

Prickles:

*Quantity.*—On main stalks from base, ordinary. On laterals from stalk, ordinary.

*Form.*—Long, hooked downward.

*Color when young.*—Green.

*Position.*—Irregular.

Small prickles:

*Quantity.*—On main stalks, none. On laterals, none.

I claim:

1. A new and distinct variety of rose plant of the hybrid tea class, substantially as herein shown and described, characterized particularly as to novelty by the unique combination of its upright, branched, stiff plant bearing large yellow-orange blooms, of little fragrance, and having glossy foliage.

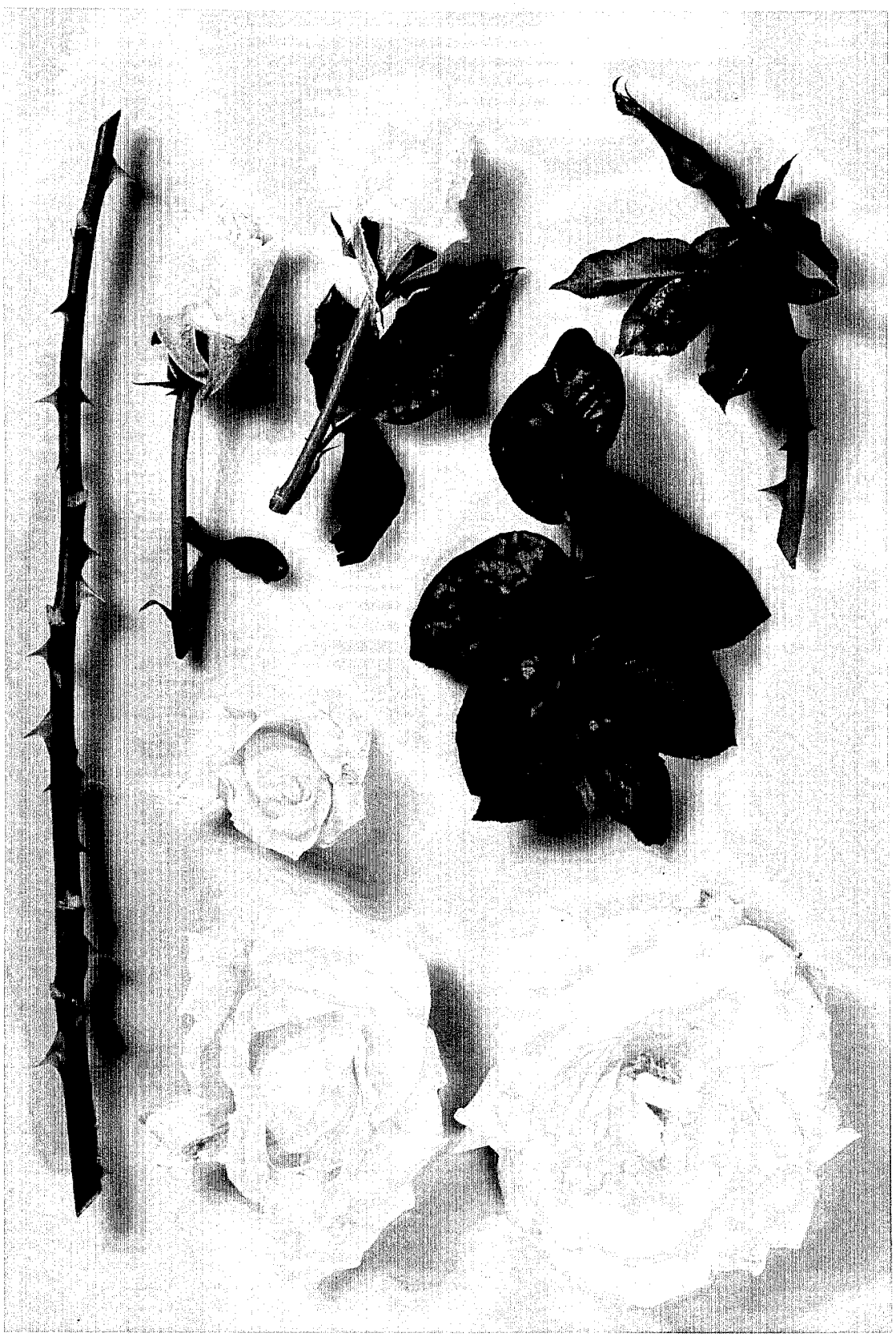

* * * * *